United States Patent [19]

Brunelle et al.

[11] Patent Number: 4,938,476
[45] Date of Patent: Jul. 3, 1990

[54] BODY POSITION ATTITUDE INDICATOR DEVICE

[76] Inventors: Timothy R. Brunelle, 2221 Marcia Ct.; Shawn Gallagher, 375 Glendening Rd., both of Orange Park, Fla. 32073

[21] Appl. No.: 406,872

[22] Filed: Sep. 12, 1989

Related U.S. Application Data

[63] Continuation of Ser. No. 202,947, Jun. 6, 1988, abandoned.

[51] Int. Cl.$^5$ ............................................. A63B 23/02
[52] U.S. Cl. ................................... 272/93; 272/DIG. 5; 128/72; 128/782; 340/573; 340/668
[58] Field of Search ................. 128/25 R, 68, 69, 721, 128/781, 782; 272/93, DIG. 4, DIG. 5; 340/573, 574, 668, 684, 686, 68 P; 200/61.45 R, 61.67, 61.68, 61.51

[56] References Cited

U.S. PATENT DOCUMENTS

| | | | |
|---|---|---|---|
| 1,870,347 | 8/1932 | Roberts | 340/689 X |
| 2,448,597 | 9/1948 | Jolley et al. | 340/689 X |
| 3,608,541 | 9/1971 | Hall | 128/781 |
| 3,634,885 | 1/1972 | Barkley | 340/573 |
| 3,831,163 | 8/1974 | Byers | 340/689 X |
| 4,196,524 | 4/1980 | Bechtel | 340/689 X |
| 4,264,899 | 4/1984 | Menzies et al. | 340/689 X |
| 4,278,854 | 7/1981 | Krause | 340/689 X |
| 4,305,058 | 12/1981 | Baumann | 340/693 X |
| 4,349,809 | 9/1982 | Tomes | 340/689 X |
| 4,516,329 | 5/1985 | Dilcox | 340/689 X |
| 4,536,755 | 8/1985 | Holzgang et al. | 340/573 |
| 4,557,275 | 12/1985 | Dempsey, Jr. | 128/782 |
| 4,617,525 | 10/1986 | Lloyd | 128/782 X |
| 4,665,388 | 5/1987 | Ivie et al. | 272/DIG. 5 X |
| 4,665,928 | 5/1987 | Linial et al. | 128/782 |
| 4,667,188 | 5/1987 | Schwartz | 340/574 X |
| 4,684,928 | 8/1987 | Takahashi et al. | 340/689 X |
| 4,737,759 | 4/1988 | Strofkay et al. | 340/689 X |

Primary Examiner—Richard J. Apley
Assistant Examiner—Joe H. Cheng
Attorney, Agent, or Firm—Thomas C. Saitta

[57] ABSTRACT

A device, worn on a part of the human body, which alerts the wearer when that body part deviates a set angular amount from true vertical, comprising a housing containing an attitude responsive switch which controls an electrical circuit. When the switch is positioned or rotated beyond a set angle, the circuit is completed and a battery activates a buzzer. The device is adjustable by rotation of the housing such that the amount of allowable deviation can be increased or decreased.

4 Claims, 2 Drawing Sheets

FIG. 4
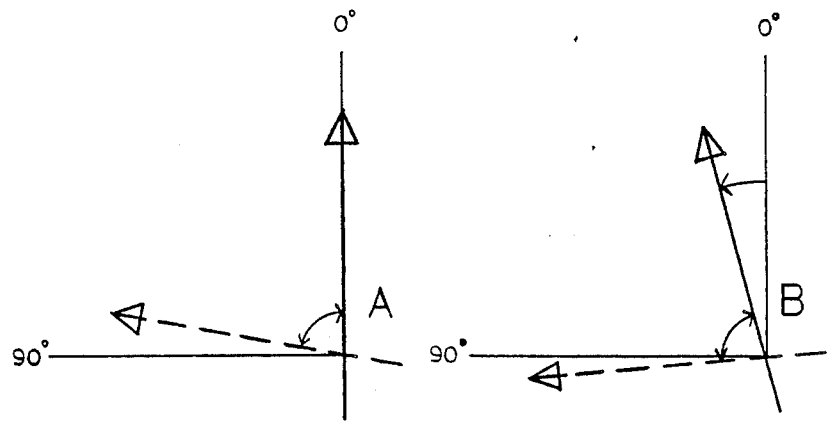
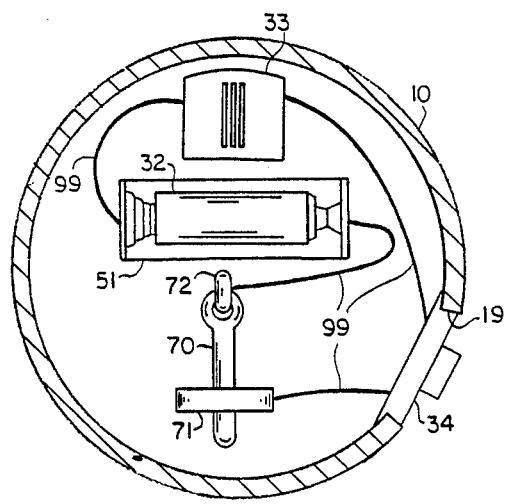
FIG. 5
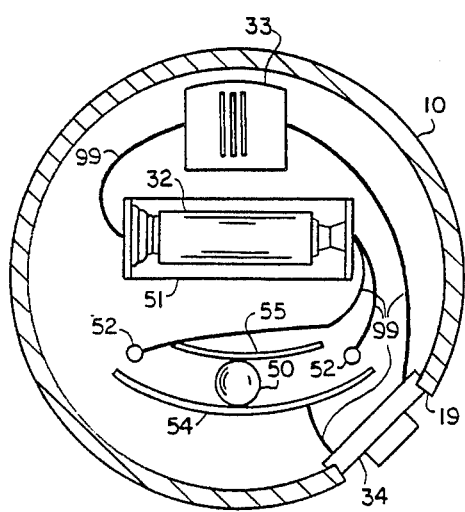
FIG. 6

4,938,476

BODY POSITION ATTITUDE INDICATOR DEVICE

This is a continuation of application Ser. No. 202,947, filed June 6, 1988, now abandoned.

BACKGROUND OF THE INVENTION

The invention relates generally to the field of body position indicator devices and more particularly to the field of devices which are worn on the body and which produce a signal in response to the angle of deviation from a set reference angle. For example, in one particular application of the invention, the device is worn on the upper torso of an individual and set to indicate when the individual bends at the waist to too great a degree, thereby causing his torso to exceed a given angle of deviation from true vertical (taken to be the line of gravitational orientation). This application of the invention will be utilized in the description of the invention.

There are situations where it is important that an individual maintain his torso in an upright position, and therefore it would be useful to have a simple, inexpensive device available to be worn on the body which will be non-obtrusive yet alert the wearer whenever his torso deviates a determined amount from true vertical position. The device would best be adjustable such that a given permissible range of movement from vertical can be individually set for each wearer.

For example, it is well known that the correct technique for lifting heavy or bulky items by hand is to bend at the knees to lower the body while maintaining a fairly erect back. In this technique, the lifting is performed by the leg muscles and does not put a strain on the spine or back muscles. This is the preferred lifting technique, since the spinal disks are susceptible to compressive injury and the back muscles are weaker and much more susceptible to injury than the leg muscles. The incorrect technique, though the technique most often used, is to bend at the waist and keep the knees straight. With this technique, the stressed leverage points are inappropriately located at the lower back rather than in the legs, and the potential for injury to the back is high. Each year, thousands of working hours are lost due to injuries directly related to improper lifting techniques, and these lost hours represent many thousands of dollars in lost productivity. The device of the invention can be used to properly train workmen in the correct lifting techniques or can be worn on the job to act as a reminder or warning when improper technique is attempted.

Another example of a setting where the device of the invention is useful is in a post-injury or post-surgery situation. It may be determined by the physician that a limited range of motion is desirable or required due to specific injuries or operations performed on an individual. The device can be set to alert the individual when this allowable range of motion is exceeded.

There are various types of devices currently in existence which relate to this field. In the physical restraint category, there are known restrictive harnesses which consist of motion limiting straps, fabric or formed material. These are worn by an individual and prevent movement beyond the allowable range. This type of device is uncomfortable, bulky, and psychologically frustrating to the wearer. In this same vein, there are known cinch belts which are worn around the waist which physically bind or dig into the skin of the wearer causing such discomfort that the wearer straightens up to the correct vertical position. The negatives of this apparatus are easily apparent.

Devices which are more distantly related are found in the posture training field. These devices often indicate poor posture or slumping rather than vertical displacement. See for example, U.S. Pat. Nos. 4,007,733 to Celeste et al and 3,670,320 to Palmer, both involving elastic tensioning devices. Badorvinac in U.S. Pat. No. 2,494,278 shows a device responsive to both frontward and rearward angular displacement of the head, consisting simply of a roller contained in a slotted housing which is worn on a hat. No adjustment is possible and the device is only suitable for head movement. Likewise, Bechtel in U.S. Pat. No. 4,196,524 teaches a more complicated device for indicating head movement. This device is worn on the top of the head and an alarm goes off if the head is dipped in any direction. None of these devices are capable of being worn on the torso to indicate angular movement out of vertical.

Finally, Leighton in U.S. Pat. No. 2,565,482 shows a device used to measure angular body movements. The device consists of a weighted pointer mounted on a pivot such that the pointer remains vertical as the device in angled. A non-pivoting dial is used to measure the angle of movement. The device only measures degree of movement and cannot be used to warn of impermissible motion.

SUMMARY OF THE INVENTION

It is therefore an object of this invention to provide a device capable of alerting an individual when a given body portion is displaced a predetermined amount from true vertical. It is a further object to provide such a device which is small, lightweight, inexpensive to produce and unobtrusive when worn. It is a further object that the device will allow for a certain permissible range of motion without production of the alert signal. It is a further object that the angle of displacement at which the device produces the alert signal be adjustable.

Briefly, the device of the invention includes a small, light-weight housing attached to a flexible material band or belt designed to comfortably encircle the wearer. In the situation where the device is used to indicate torso movement, the device is worn at a point above the waist. The housing is worn on the side. The housing contains an alert means, such as a buzzer or a light, and means such as a battery to power the alert means. Placed in the circuit between the power means and the alert means is an attitude-responsive contact switch mechanism, such as a mercury switch, which consists of a tubular container having two circuit leads extending into the interior of the tube at one end. These leads are separated a short distance. Contained in the tube is a small amount of conductive mercury. When the wearer leans his torso forward, the tube is slanted such that the mercury flows to the end with the two leads, the circuit is completed and the alert means is activated. As long as the tube is slanted in the opposite direction, the mercury will not contact the leads and the circuit is broken. An on/off switch can also be incorporated in the circuit to disengage the circuit when the device is not in use. The housing is adjustable relative to the belt, so that the point at which the mercury flows forward to contact the leads can be adjusted to allow different permissible angular displacement amounts to accommodate individual differences. These features, the best mode and embodiment will be explained in greater detail later.

BRIEF DESCRIPTION OF THE DRAWINGS

FIG. 4 is a graphic illustration of the reference lines for torso and device in two positions.

FIG. 5 is an illustration of an alternate embodiment of the invention, where the mercury switch is replaced by a pendulum switch.

FIG. 6 shows still another embodiment of the invention, where a ball bearing switch is used.

DETAILED DESCRIPTION OF THE INVENTION

Figure 1:
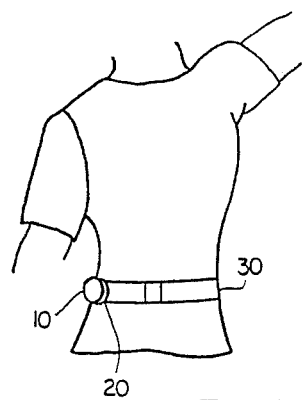
FIG. 1 is an exterior perspective view of one embodiment of the invention showing the positioning of the belt when worn by an individual.

The invention may best be described with reference to FIGS. 1, 2, and 3. As previously discussed, the invention produces a signal to alert the wearer when his torso exceeds a given angle from vertical. For example, the device may be set such that the alert signal is produced when the wearer bends forward any amount beyond 20 degrees from true vertical. As shown in FIG. 1, the device comprises a small housing 10 which is attached by a plate 20 to belt or band 30. The invention is worn at a point slightly above the waist, with the housing situated to one side of the wearer. With this positioning, the device will respond to the amount of forward bend of the wearer's upper body.

Figure 2:
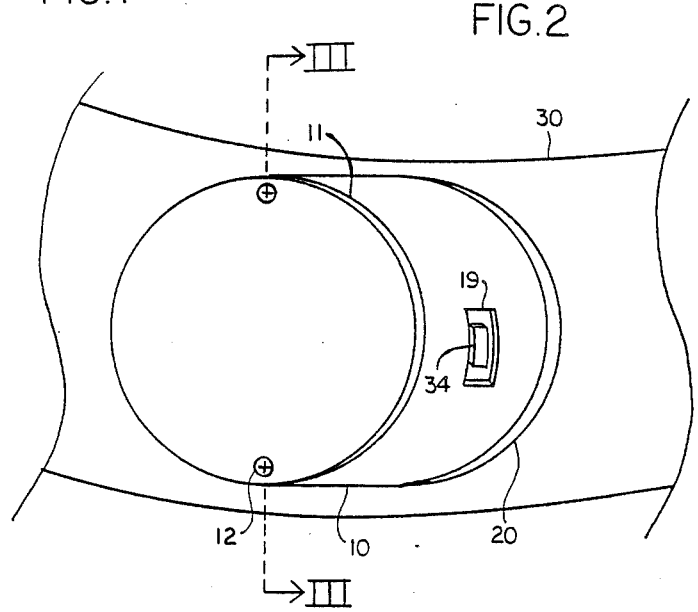
FIG. 2 is an exterior perspective of one embodiment of the invention.

Referring now the FIG. 2, the relationship of the belt 30, plate 20 and housing 10 can better be seen. The belt 30 can be made of any material suitable for comfortable wear on the body. It may be relatively wide, for example four or five inches, so that it will maintain its position on the body and adequately support housing 10 without twisting or sliding. Possible materials include cloth, plastic, leather, foam, etc. Any common fastener device common to belts may be used to fasten the belt 30 around the wearer.

Plate 20 is attached to belt 30 by suitable fastening means or adhesive. Plate 20 is attached such that it is permanently fixed in one position. Plate 20 is preferably circular in shape, of a size equal to the diameter of housing 10. The back wall of housing 10 is fastened to plate 20 by a single rivet 77 located at the center of the circular plate 20 and housing 10. The housing 10 is riveted so that it is able to be rotated on its central axis in relation to the fixed plate 20. To set the angle at which the device produces the alert, housing 10 is rotated to the desired position relative to true vertical and then secured by a screw (not shown) extending through plate 20 into one of a series of indentations in the rear wall of housing 10. To readjust the device, the screw is loosened, the housing 10 is rotated and the screw is tightened.

Housing 10 is preferable circular, although other shapes are possible. Housing 10 is a closed tube, approximately three inches in diameter and approximately one inch thick. The main body of housing 10 is a short tube closed on one end, thereby forming a cavity to receive individual components of the device. A lid 11 is fastened by suitable means, such as screws 12, such that it can be removed if replacement of any of the individual components is required. Housing 10 can be composed of any hard, rigid material.

Figure 3:
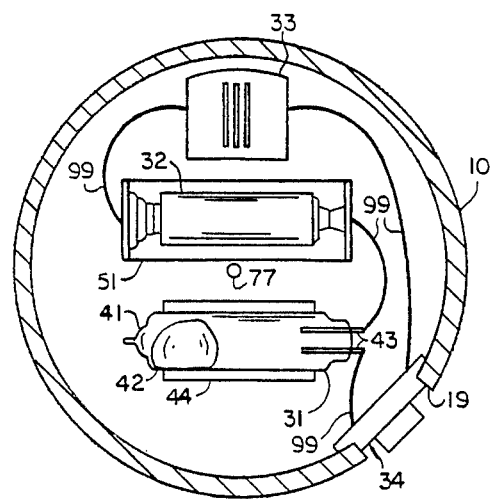
FIG. 3 is a sectional view, taken substantially along line III—III of FIG. 2, such that one side of the housing is not shown and the interior elements are exposed.

FIG. 3, a cross-section of housing 10, shows a similar view to that of the view when lid 11 is removed to expose the individual components. The main individual components, all connected in an electrical circuit, are mercury switch 31, power means 32, alert means 33 and activation switch 34. Each of these components will now be individually described.

Mercury switch 31 is a known switch adaptable for many uses. It consists of a sealed glass tube 41 which contains a small amount of conductive mercury 42. At one end of mercury switch 31 two electrical leads 43 extend from the exterior of the glass tube 42 into the interior. The leads 43 do not physically contact, being separated by a short distance. When the tube 41 is slanted downward on the end containing the leads 43, mercury 42 flows to that end of glass tube 41. The amount of mercury 42 is sufficient to bridge the gap between leads 43, thereby enabling an electric current to pass from one lead 43 to the other. Mercury switch 31 is fastened to the rear of housing 10 by retaining clip 44 or suitable adhesive.

A power means 32 is contained in housing 10. This is preferably a small battery of the ordinary type. The power means 32 need merely supply enough power to operate alert means 33. The power means 32 is also secured to the rear of housing 10 by a suitable bracket 51 having connectors to allow wires 99 to be fastened. Alert means 33 can be of any type of small, low power component which produces a signal. In the preferred mode, alert means 33 is a buzzer, although any other sound or light producing mechanism can be substituted. Activation switch 34 can be of any common type of on/off switch, such as a sliding contact or push button contact, which can be set in a non-conducting or conducting mode. This enables the wearer to deactivate the device when not in use. Activation switch 34 is fastened by suitable means or mechanically slotted into the wall of housing 20 at aperture 19 so that it is externally accessible without having to remove housing 10 from bracket 20.

Finally, all of the individual components are serially connected by wires 99, attached in known manner such as by soldering or clips, to form one complete electrical circuit having two possible points of interruption—one at activation switch 34 and the other at the gap between leads 43 of mercury switch 31. Thus, when activation switch 34 is in the on or conducting position, alert means 33 will be activated only when mercury 42 bridges the gap between leads 43.

In operation, the device works as follows. The device is worn so that bracket 20 and housing 10 are on the wearer's side at a point above the waist. It is preferable to wear the device as high as is comfortable, as this puts it a distance from the major bending point located at the waist. Housing 10 is positioned on plate 20 such that the central axis of mercury switch 31 is slightly above parallel to a horizontal line directly forward of the wearer. Mercury switch 31 is positioned with the leads 43 to the front of the wearer. In this position, with the wearer standing upright (i.e., approximately near true vertical), the mercury 42 will remain in the rear of tube 41, away from leads 43, and the circuit is not completed. As the wearer bends forward at the waist, the central axis of mercury switch 31 approaches and then passes through horizontal (i.e., 90 degrees from vertical). Upon passing through horizontal, the front of mercury switch 31 will now be lower than the rear, mercury 42 will flow forward, completing the circuit and activating alert means 33. Upon the wearer straightening his torso, the central axis will return through horizontal, mercury 42 will flow away from leads 43 and the circuit will be broken.

The relationship of mercury switch 31 to torso position and true vertical is graphically illustrated in FIG. 4. At position A, the wearer's torso is upright, at or near vertical, as shown by the solid arrow. The central axis of mercury switch 31, shown by the dashed arrow, is ten degrees above horizontal. Thus, in this example the permitted range of motion is ten degrees off vertical. As the wearer leans forward fifteen degrees to position B, the central axis of mercury switch 31 passes through horizontal and mercury 42 flows forward, causing the alert to be activated.

In FIG. 4, the central axis of mercury switch 31 is 10 degrees above horizontal allowing only 10 degrees of forward motion. The attitude of housing 10 within bracket 20 determines the degrees from horizontal of the central axis of mercury switch 31. By rotating housing 10 within bracket 20, the allowed range of forward motion is adjusted for specific individual circumstances. For example, if 30° degrees of forward motion off vertical was determined to be the permissible range, the central axis of mercury switch 31 is set at 30° off horizontal. Thus, after 30° of forward motion, the axis will pass through horizontal and the alert means 33 will be activated. This adjustment is made by loosening the setting screw on the rear of housing 10, rotating housing 10 to the desired position and retightening the screw to secure housing 20 in place.

While reference has been made above to forward range of motion, it should be obvious that this is a relative term and that backward motion out of vertical can be indicated by the device simply by affixing it to the torso or body part in the reverse direction.

In another embodiment, the mercury switch described above may be replaced with alternate attitude-responsive contact mechanisms. For example, the switch may be replaced by a pendulum switch, as shown in FIG. 5. This switch consists of a hanging, free swinging vertical pendulum 70 which is one lead. The other lead for the circuit can be a pin, plate, two plates or an annular ring, made of suitable electrical conducting material, positioned so that the pendulum will make contact when it swings out of vertical a sufficient amount. This set up allows for measurement of forward position, forward and backward position or position out of vertical in any direction. In FIG. 5 an annular ring is shown. Pendulum 70 is fastened to the back wall of housing 10 by an eyebolt 72 or other suitable means which allows pendulum 70 to freely swing in all directions. If only a single contact pin, plate or two plates are used, then pendulum 70 need only swing in one directional plane. Conductive ring 71 is also fastened to the back wall of housing 10 by suitable mechanical or adhesive means. Wires 99 are now connected, one to the conducting ring 71 and the other to pendulum 70. Thus, when activation switch 34 is in the conducting position, the only break in the circuit occurs between pendulum 70 and conducting ring 71. When the wearer moves the device out of true vertical a given amount, pendulum 70 will contact conducting ring 71 and the alert will be given. The device can be adjusted for different ranges of allowable motion by positioning the ring higher or lower in relation to the pendulum.

In still another embodiment, shown in FIG. 6, the mercury switch may be replaced by a ball bearing type electrical contact. Here, a conductive ball bearing 50 is placed in a curved channel 55 lower in the center than at its ends. The bottom of the channel contains a conductive plate 54 such that the ball bearing 50 is in continuous contact with this plate. At one end or at both ends, a conducting pin or set of pins 52 is positioned such that whenever the bearing 50 rolls to the end of the channel due to the wearer bending, the circuit is completed between the conducting plate 54 and pin 52, one wire 99 being connected to conducting plate 54 and the other wire 99 being connected to one or both pins 52.

Both these just described embodiments enable the alert signal to be produced in both the forward and backwards position, but both can be too sensitive to incidental motion or jarring. It may be necessary to further adapt the invention to include damping means to overcome this problem. One adaption is to house the pendulum or ball bearing mechanism inside a small, closed container inside housing 10, the container being filled with a viscous, non-conducting damping fluid, such as oil. In this embodiment, the device must be maintained in the position beyond the predetermined angle out of vertical a sufficient period of time before the contacts will come together, since the viscous fluid will slow the motion of the pendulum or ball bearing, and therefore the alert signal will not be produced by simple jarring.

The above descriptions and illustrations are by way of example only are not to be taken as limiting the invention in any manner. It is obvious that one skilled in the art can substitute known equivalents for the structures and means described. The full scope and definition of the invention, therefore, is to be as is set forth in the following claims.

We claim:
1. A device worn on a human torso for indicating torso bending at the waist by producing an audible signal, said device comprising in combination:
   (A) body attachment means comprising a band to encircle and maintain a cylindrical housing on the side of a human torso, such that the central axis of the cylindrical housing is perpendicular to the vertical axis of the torso;
   (B) a plate permanently fastened to said band to receive the cylindrical housing; and
   (C) the cylindrical housing rotatably attached to said plate by a centrally positioned rivet allowing rotation of said housing about the central axis of said housing relative to said plate, said housing containing an electrical circuit housing,
   power means comprising a battery to supply electrical current to an alert means,
   alert means to produce an audible signal,
   an activation switch to turn the device off and on, and
   an attitude responsive switch to open and close said electrical circuit, directly affixed to said housing, where said attitude responsive switch is positioned in the electrical circuit between said power means and said alert means, said attitude responsive switch allowing said current to reach said alert means to produce said signal only when torso bending at the waist occurs to alter the attitude of said housing, and where said attitude responsive switch is adjustable relative to said torso only by rotating said housing relative to said plate.

2. The device of claim 1, where said attitude responsive switch is a mercury switch.

3. The device of claim 1, where said attitude responsive switch is a pendulum switch.

4. The device of claim 2, where said attitude responsive switch is a ball bearing switch.

* * * * *